US010172521B2

(12) United States Patent
Goldhaber

(10) Patent No.: US 10,172,521 B2
(45) Date of Patent: Jan. 8, 2019

(54) SYSTEMS AND METHODS FOR TRACKING IMAGING ATTENUATORS

(71) Applicant: General Electric Company, Schenectady, NY (US)

(72) Inventor: David M. Goldhaber, Shorewood, WI (US)

(73) Assignee: General Electric Company, Schenectady, NY (US)

( * ) Notice: Subject to any disclaimer, the term of this patent is extended or adjusted under 35 U.S.C. 154(b) by 367 days.

(21) Appl. No.: 13/936,767

(22) Filed: Jul. 8, 2013

(65) Prior Publication Data

US 2015/0011865 A1  Jan. 8, 2015

(51) Int. Cl.
| | |
|---|---|
| *A61B 5/00* | (2006.01) |
| *A61B 5/055* | (2006.01) |
| *A61B 6/03* | (2006.01) |
| *G01R 33/48* | (2006.01) |
| *A61B 6/00* | (2006.01) |

(52) U.S. Cl.
CPC ............ *A61B 5/0035* (2013.01); *A61B 5/055* (2013.01); *A61B 6/037* (2013.01); *A61B 6/4417* (2013.01); *A61B 6/5205* (2013.01); *A61B 6/5247* (2013.01); *G01R 33/481* (2013.01)

(58) Field of Classification Search
None
See application file for complete search history.

(56) References Cited

U.S. PATENT DOCUMENTS

| | | | |
|---|---|---|---|
| 4,254,778 | A | 3/1981 | Clow et al. |
| 4,572,198 | A | 2/1986 | Codrington |
| 4,613,837 | A | 9/1986 | Blass et al. |
| 4,638,252 | A | 1/1987 | Bradshaw |

(Continued)

FOREIGN PATENT DOCUMENTS

| | | |
|---|---|---|
| DE | 3937052 | 5/1990 |
| EP | 0385367 | 10/1995 |

OTHER PUBLICATIONS

Slyper et al., "Sensing through structure: designing soft silicone sensors." Proceedings of the fifth international conference on Tangible, embedded, and embodied interaction. ACM, 2011.*

*Primary Examiner* — Katherine Fernandez
*Assistant Examiner* — Marjan Saboktakin
(74) *Attorney, Agent, or Firm* — Dean D. Small; The Small Patent Law Group, LLC

(57) ABSTRACT

A system for imaging an object is provided including a first imaging acquisition module, a magnetic resonance imaging (MRI) acquisition module, and a first reconstruction module. The first imaging acquisition module is configured to acquire imaging information using a first non-MRI modality. The MRI acquisition module is configured to acquire MR non-imaging, foreign structure (NFIS) information. The MR NFIS information is acquired via at least one tracking coil associated with an external non-therapeutic (ENT) structure. The MR NIFS information corresponds to at least one of a position or orientation of the ENT structure. The first reconstruction module is configured to obtain the MR NIFS information and use the MR NIFS information to correct an attenuation in the imaging information acquired by the first imaging acquisition module associated with the ENT structure.

17 Claims, 5 Drawing Sheets

(56) References Cited

U.S. PATENT DOCUMENTS

| | | |
|---|---|---|
| 4,672,972 A | 6/1987 | Berke |
| 4,799,015 A | 1/1989 | Sepponen |
| 4,889,127 A | 12/1989 | Takeda et al. |
| 4,962,763 A | 10/1990 | Sato et al. |
| 4,966,149 A | 10/1990 | Stokar |
| 4,989,608 A | 2/1991 | Ratner |
| 4,995,394 A | 2/1991 | Cline et al. |
| 5,005,592 A | 4/1991 | Cartmell |
| 5,042,486 A | 8/1991 | Pfeiler et al. |
| 5,099,845 A | 3/1992 | Besz et al. |
| 5,107,862 A | 4/1992 | Fabian et al. |
| 5,170,789 A | 12/1992 | Narayan et al. |
| 5,271,400 A | 12/1993 | Dumoulin et al. |
| 5,307,808 A | 5/1994 | Dumoulin et al. |
| 6,492,814 B1 * | 12/2002 | Watkins et al. ............... 324/318 |
| 7,450,985 B2 * | 11/2008 | Meloy .................. A61B 5/0555 128/870 |
| 2008/0033278 A1 * | 2/2008 | Assif ...................... A61B 5/055 600/410 |
| 2008/0097191 A1 * | 4/2008 | Dumoulin ............ G01R 33/287 600/422 |
| 2009/0105583 A1 * | 4/2009 | Martin et al. ................. 600/422 |
| 2009/0289633 A1 * | 11/2009 | Dutto et al. .................. 324/321 |
| 2010/0312096 A1 * | 12/2010 | Guttman ................ A61B 5/415 600/411 |
| 2010/0317962 A1 * | 12/2010 | Jenkins .................. A61B 5/055 600/411 |

\* cited by examiner

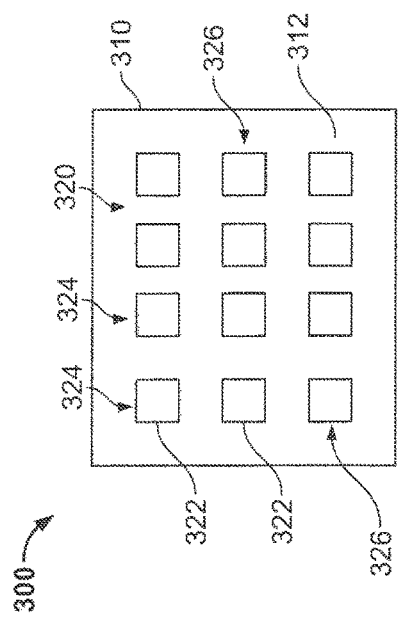

SYSTEMS AND METHODS FOR TRACKING IMAGING ATTENUATORS

BACKGROUND OF THE INVENTION

The subject matter disclosed herein relates generally to dual modality imaging systems, and more particularly to systems and methods for utilizing magnetic resonance (MR) tracking coils to address attenuations in imaging information acquired via a non-MR modality, such as positron emission tomography (PET).

Dual modality or multi-modal imaging may be utilized to obtain the benefits or advantages of two or more imaging modalities or techniques. For example, PET imaging and MR imaging may be utilized in a dual modality imaging system. However, such dual modality imaging may provide certain drawbacks or challenges.

For example, simultaneous or concurrent PET/MR imaging may result in the placement of devices such as surface or receive coils, patient support equipment, patient positioning equipment, or the like between the patient and the PET detectors. Such objects may significantly attenuate, for example, 511 keV photons, and may contribute to significant PET image artifacts and quantitation errors. To account for the attenuation of such equipment, the position and orientation of the equipment must be known or determined. Such equipment may be invisible to standard PET and MR imaging techniques, however. This problem may be exacerbated when the equipment is movable or articulable, and thus may not be accounted for using a priori knowledge of an initial position and orientation. Further, use of fiducial markers (e.g., fiducial markers in an MR image) to identify such equipment on an image has drawbacks as well. For example, MR images provide relatively low geometric fidelity and accuracy. Further still, fiducial markers may have a negative impact on the quality of the image in which the fiducial markers appear.

BRIEF DESCRIPTION OF THE INVENTION

In accordance with various embodiments, a system for imaging a portion of a patient within a field of view (FOV) of a system is provided. The system includes a first imaging acquisition module, a magnetic resonance imaging (MRI) acquisition module, and a first reconstruction module. The first imaging acquisition module is configured to acquire imaging information for the portion of the patient within the FOV using a non-MRI first modality. The MRI acquisition module is configured to acquire magnetic resonance (MR) information associated with an external non-therapeutic (ENT) structure with in the FOV that includes MR non-imaging, foreign structure (NIFS) information associated with the ENT structure. The MR NIFS information is acquired via at least one tracking coil associated with the ENT structure. The MR NIFS information corresponds to at least one of a position or orientation of the ENT structure. The first reconstruction module is configured to reconstruct an image using the imaging information acquired by the first imaging acquisition module. The first reconstruction module is also configured to obtain the MR NIFS information, and to use the MR NIFS to correct an attenuation associated with the ENT structure.

In accordance with various embodiments, a method of imaging an object is provided. The method includes acquiring, with a first imaging acquisition module, first imaging information corresponding to a non-MRI first modality. The method also includes acquiring, with a magnetic resonance imaging (MRI) acquisition module, magnetic resonance (MR) non-imaging, foreign structure (NIFS) information associated with an external non-therapeutic (ENT) structure. The MR NIFS is acquired via at least one tracking coil associated with the ENT structure. The MR NIFS information corresponds to at least one of a position or orientation of the ENT structure. Also, the method includes addressing an attenuation in the first imaging information associated with the ENT structure to produce corrected first imaging information. The attenuation is addressed using the MR NIFS information. The method also includes reconstructing, with a first reconstruction module, an image using the corrected first imaging information.

In accordance with various embodiments, a tangible and non-transitory computer readable medium is provided. The computer readable medium includes one or more computer software modules configured to direct one or more processors to obtain first imaging information corresponding to a non-MRI first modality. The one or more computer software modules are also configured to direct the one or more processors to obtain magnetic resonance (MR) non-imaging, foreign structure (NIFS) information associated with an external non-therapeutic (ENT) structure, wherein the MR NIFS information is acquired via at least one tracking coil associated with the ENT structure. The MR NIPS information corresponds to at least one of a position or orientation of the ENT structure. Also, the one or more computer software modules is configured to direct the one or more processors to address an attenuation in the first imaging information associated with the ENT structure to produce corrected first imaging information. The attenuation is addressed using the MR NITS information. Further, the one or more computer software modules are configured to direct the one or more processors to reconstruct an image using the corrected first imaging information.

BRIEF DESCRIPTION OF THE DRAWINGS

FIG. 3 is a front view of a tracking coil system in accordance with various embodiments.

FIG. 4 is a side view of the tracking coil system of FIG. 3 in a first position.

FIG. 5 is a side view of the tracking coil system of FIG. 3 in a second position.

DETAILED DESCRIPTION OF THE INVENTION

Figure 1:
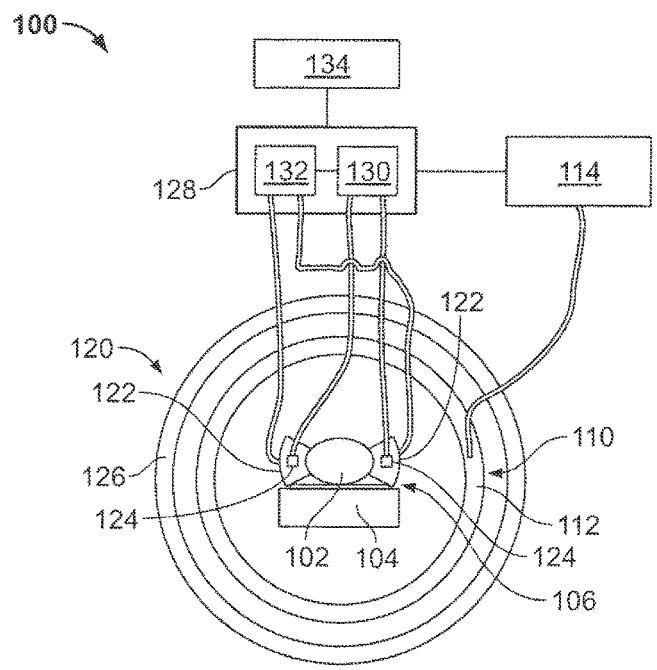
FIG. 1 is a schematic view of a dual modality imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "image" or similar terminology is not intended to exclude embodiments in which data representing an image is generated, but a viewable image is not. Therefore, as used herein the term "image" broadly refers to both viewable images and data representing a viewable image. However, certain embodiments generate, or are configured to generate, at least one viewable image.

Various embodiments provide systems and methods for imaging an object, such as a patient. In various embodiments, imaging data acquired via a first modality (e.g., PET, SPECT) is corrected to account for attenuations that are not visible via the first modality. For example, objects such as pads, supports, or measurement equipment may attenuate imaging data, but may not be detectable by or visible to a PET or SPECT system. In various embodiments, MR tracking coils may be employed to determine the position of attenuating bodies, with the determined positions used to correct the imaging data of the first modality. In various embodiments, MR tracking coils may provide information that is used to account for attenuations of objects placed external to an object or patient, but may not be configured to provide imaging information for reconstruction of an MR image.

A technical effect of at least some embodiments is improving correction for attenuation in a first imaging modality (e.g., PET, SPECT) caused by structures or devices that are not visible via the first imaging modality. A technical effect of at least some embodiments is improved quantitation accuracy, for example in PET imaging. A technical effect of at least some embodiments is the reduction of artifacts in images. A technical effect of at least some embodiments includes utilizing a relatively quick (e.g., about 1 second) MR information acquisition to locate attenuating material (e.g., PET attenuating material) with high (e.g., within about one millimeter) accuracy.

FIG. 1 illustrates a schematic view of a dual modality imaging system 100 formed in accordance with various embodiments. The dual modality imaging system 100 may be configured to acquire imaging information and/or reconstruct images using two or more imaging modalities (e.g., positron emission tomography (PET), computed tomography (CT), single photon computed emission tomography (SPECT), or magnetic resonance imaging (MRI), among others). For example, the depicted embodiment includes a first imaging acquisition system 110 (or first imaging acquisition module) and a MRI acquisition system 120 (or MRI acquisition module). For additional details on particular modalities, an example of an MRI imaging system including additional details is discussed herein in connection with FIG. 7, and an example of a PET imaging system including additional details is discussed herein in connection with FIG. 8. Returning to FIG. 1, the illustrated dual modality imaging system 100 is configured to image an object 102 that is supported on a table 104. Additionally, one or more external non-therapeutic structures 106 are disposed proximate the object 102 within a field of view of at least one of the first imaging acquisition system 110 and the MRI acquisition system 120.

As used herein, an external structure, body, or device, may be understood as a structure that is configured to remain outside of the object 102 being imaged during an entirety of an imaging procedure, in contrast to a structure, body, or device configured to be inserted within the object 102. For example, in some embodiments, the object 102 to be imaged may be a human patient, or a portion thereof. Examples of external structures include pads or supports, among others. Examples of internal structures include catheters, syringes, or surgical instruments configured to have all or a portion thereof inserted into a patient. A non-therapeutic structure or device as used herein may be understood as a structure or device that is not configured to deliver a therapy or to be utilized to directly perform a therapeutic process or procedure on a patient. By way of example, non-therapeutic structures or devices may include pads, supports, audio-visual systems, or measuring or detection devices, for example. For purposes of clarity and avoidance of doubt, therapeutic structures or devices may include syringes; surgical instruments such as scalpels, retractors, clamps, or the like; or ablation devices (e.g., ultrasonic ablation devices), among others. The external non-therapeutic structures 106 are not integral to the MRI acquisition system 120 housing, nor part of the first (e.g., PET) acquisition system 110 housing. The external non-therapeutic structures 106 may be separate and distinct from (and moveable in various directions or orientations with respect to) the housing of the MRI system and the first imaging system. For example, the external non-therapeutic structures 106 may be configured as MR surface coils, patient supports, and/or positioning pads.

In various embodiments, external non-therapeutic structures 106 may be configured for one or more various beneficial purposes during an imaging procedure, such as patient comfort or detection. For example, in the illustrated embodiment, the depicted external non-therapeutic structures 106 are configured as receive coil modules 122 that include MRI receive coils disposed within a padded structure configured for placement against the object 102 (e.g., a patient or portion thereof). Additionally or alternatively, in various embodiments, the external non-therapeutic structures 106 may include, for example, one or more of pads or other structures configured for patient support and/or comfort; audio-visual systems and/or components configured for patient comfort, entertainment, or relaxation; imaging detection system or components (e.g., one or more MRI receive coils); or gating measurement equipment or devices (e.g., one or more of electrocardiogram (ECG) measurement devices, devices for measuring or detecting breathing, motion detection devices, or the like).

One drawback of use of such external non-therapeutic structures is that the structures may act as an attenuator to one or more modalities while not being visible to one or more modalities. In various embodiments, MR tracking coils may be mounted, affixed, or otherwise associated with one or more external non-therapeutic structures to help determine a position and/or orientation of the one or more external non-therapeutic structures, and to use the determined position and/or orientation to correct an image or otherwise account for an attenuation caused by the one or more external non-therapeutic structures in a non-MR modality, such as PET.

As indicated above, the dual modality imaging system 100 includes a first imaging system 110 and a MR imaging system 120. As also indicated above, the first imaging system 110 may be configured to obtain imaging information corresponding to a first non-MRI modality, and to reconstruct an image using the obtained imaging information corrected for attenuations by MR information collected by the MR imaging system 120. As one example, as depicted in FIG. 1, the first imaging system 110 may be configured as a PET imaging system. As also shown in FIG. 1, the first imaging system 110 and the MR imaging system 120 may be disposed in an overlapping orientation. For example, one or more portions of the MR imaging system 120 (e.g., receive coils) may be disposed within a field of view of the first imaging system 110, with one or more other portions of the MR imaging system 120 (e.g., primary coil) disposed outside of the field of view of the first imaging system 110. Alternative or additional modalities (e.g., CT or SPECT, among others) may be utilized in various embodiments.

PET imaging systems typically generate images depicting the distribution of positron-emitting nuclides in patients based on coincidence emission events detected using a detector system, usually configured as a ring assembly of detector blocks. The positron interacts with an electron in the body of the patient by annihilation, and then the electron-positron pair is converted into two photons. The photons are emitted in opposite directions along a line of response. The annihilation photons are detected by detectors on both sides of the line of response of the detector ring. The image is then generated based on the acquired emission data that includes the annihilation photon detection information.

Returning to FIG. 1, the depicted first imaging system 110 includes a PET acquisition module 112, and a PET reconstruction module 114. The PET acquisition module 112 provides an example of a first acquisition module and the PET reconstruction module 114 provides an example of a first reconstruction module. Generally, the PET reconstruction module 114 obtains PET imaging information from the PET acquisition module 112, and corrects or otherwise adjusts the PET imaging information using information obtained from the MR imaging system (e.g., information from MR tracking coils associated with one or more external non-therapeutic structures 106). The PET reconstruction module 114 may then utilize the corrected PET imaging information (e.g., corrected to account for attenuation from one or more external non-therapeutic structures 106, and/or internal or anatomical sources of attenuation) to reconstruct an image. In various embodiments, the PET reconstruction module 114 may also use MR imaging information that has been registered with PET imaging information to reconstruct a hybrid image.

In the illustrated embodiment, the PET acquisition module 112 is configured as a ring of detectors. The object 102 to be imaged is disposed within the inside or field of view of the ring of the PET acquisition module 112. As seen in FIG. 1, the external non-therapeutic structures 106 are also within the field of view of the ring of the PET acquisition module 112 and thus may be cause attenuation of PET imaging information regarding the object 102 obtained by the PET acquisition module 112. In the illustrated embodiment, the external non-therapeutic structures 106 are configured as MR surface coil modules 122. A tracking coil module 124 is affixed to, mounted to, or otherwise associate with each MR surface coil module 122. Alternatively or additionally, the external non-therapeutic structures 106 may include, for example, patient comfort pads or audio-visual equipment disposed within the field of view of the PET acquisition module 112, with a tracking coil module 124 affixed to, mounted to, or otherwise associated with each external non-therapeutic structure 106.

The depicted PET reconstruction module 114 obtains PET imaging information from the PET acquisition module 112, and also obtains information from the MR imaging system 120 as well. The PET reconstruction module 114 corrects the obtained PET imaging information for one or more attenuations indicated by or corresponding to information from the MR imaging system 120. For example, the MR imaging system 120 may provide information corresponding to the external non-therapeutic structures 106. In various embodiments, the MR imaging system may provide information corresponding to the position and orientation of an external non-therapeutic structure 106 (e.g., as determined using information from a MR tracking coil module 124). The attenuation properties for the external non-therapeutic structure 106 may be stored in a database included in the PET reconstruction module 114 (e.g., a database stored in a memory of the PET reconstruction module 114) or accessible to the PET reconstruction module 114. In other embodiments, the attenuation properties for the external non-therapeutic structure 106 may be stored in a database included in the MR imaging system 120 or otherwise accessible to the MR imaging system 120, with the attenuation information provided to the PET reconstruction module 114 along with the information corresponding to the position and/or orientation of the external non-therapeutic structure determined using the MR tracking coil module 124.

Using the information corresponding to the position and orientation of the external non-therapeutic structure 106 as well as the information corresponding to the attenuation properties of the external non-therapeutic structure 106, the PET reconstruction module 114 may correct the PET imaging information to account for attenuation due to the external non-therapeutic structure 106. The process may be performed for each external non-therapeutic structure 106. Further, in various embodiments, the PET reconstruction module 114 may obtain MR imaging information (e.g., information corresponding to internal structures of a patient that may have attenuating effect on PET imaging information) from the MR imaging system 120 and correct the PET imaging information to account for attenuation due to internal structures or anatomy.

The depicted MR imaging system 120 is configured to obtain MR imaging information and MR non-imaging information, and to reconstruct an MR image using the MR imaging information. The MR non-imaging information may be non-patient information and correspond to a foreign structure, and be understood as non-imaging, foreign structure (NIFS) information. For example, the foreign structure may be an external non-therapeutic device that is not a part of an object being imaged nor an integral part of a housing of an imaging system. MRI systems generally include a magnet to create a main magnetic field with gradient magnets exciting magnetic moments within the main magnetic field to acquire MRI data. Further, such systems also typically include a number of radio-frequency (RF) coils for receiving the MRI data that is provided to a processing unit for forming an image. As used herein, MR imaging information includes information obtained via an MR detection system that is used to provide a primary image intended to be viewed by a human observer. As used herein, MR non-imaging information includes information obtained via an MR detection system that is used to generate a secondary or tracking "image" not intended or configured for viewing, but instead configured to be used to correct attenuations, for example, for external non-therapeutic structures. Thus, in various embodiments, the MR non-imaging information thus may not be reconstructed into an image configured for viewing, but instead may be used to modify MR imaging information (and/or PET imaging information, for example) that in turn is reconstructed into a viewable image.

As shown in FIG. 1, the MR imaging system. 120 includes surface coil modules 122, tracking coil modules 124, an MR analysis module 128 and an MR reconstruction module 134. In the illustrated embodiment, the surface coil modules 122 are an example of external non-therapeutic structures 106, with each surface coil module 122 having a tracking coil module 124 affixed thereto. Generally, in various embodiments, the MR analysis module 128 obtains MR imaging information via the surface coil modules 122 and MR non-imaging information (e.g., information corresponding to the position and/or orientation of one or more external non-therapeutic structures 106) via the tracking coil modules 124. The MR analysis module 128 may be configured to provide the MR non-imaging information to the first imaging system 110 (e.g., to the PET reconstruction module 114). The MR non-imaging information may be provided in a raw configuration (e.g., as obtained from the tracking coil modules 124), or may be provided in a processed form. For example, the MR analysis module 128 may process the information obtained from the tracking coil modules 124 to determine a position and orientation of one or more external non-therapeutic structures 106, and to provide the position and orientation for each external non-therapeutic structure 106 along with information corresponding to the attenuation for the particular external non-therapeutic external structure 106.

The surface coil modules 122 of the illustrated embodiment are configured to obtain MR imaging information and to provide the MR imaging information to the MR analysis module 128. In various embodiments, each surface coil module 122 may include one or more surface or RF receive coils embedded within or otherwise associated with a pad. The pad, for example, may be configured for placement against a patient and/or support for a patient or for a coil against a patient. The pad may be substantially rigid in some embodiments, or may be deformable in other embodiments. In various embodiments, a structure including RF receive coils may include one or more portions that are articulable with respect to other portions.

The tracking coil modules 124 in the illustrated embodiment are mounted to, affixed to, or otherwise associated with the external non-therapeutic structures 106, and are configured to provide information regarding the position and/or orientation of the external non-therapeutic structures 106. For example, a given tracking coil module 124 may include a plurality of tracking coils arranged in fixed relation to an external non-therapeutic structure 106. The location of each individual coil of the tracking coil module 124 may be determined, and the combination of locations of individual coils may be used to determine the position and/or orientation of an external non-therapeutic structures. For example, three or more locations may be used to identify the position and orientation of a rigid body. Additional coils and/or coil modules may be used to determine the position and/or orientation of structures that are deformable or articulable.

In various embodiments, each tracking coil module 124 may include one or more tracking coils, with each tracking coil in turn including an enclosed volume of liquid surrounded by a coil. For example, each tracking coil may include a small or "micro" MR receiver coil that includes a small MR-visible sample, such as an enclosed volume of mineral oil. These small or micro coils sensitively receive the MR signal produced by the enclosed volume of fluid when exposed to a magnetic field of the MR imaging system 120, but are relatively insensitive to signals produced outside the enclosed volume. For a given micro coil, a non-selective excitation followed by a readout performed in one of the cardinal directions produces a signal with frequency content corresponding to the position of the sample in the enclosed volume in the read direction. A series of such excitations and readouts serves to locate each sample and corresponding micro-coil in 3-dimensional space. For example, a mapping between frequency and position may be achieved by performing a 1D Fourier transform and then using detailed knowledge of the field created by each readout gradient coil. In this way, the locations of the samples are determined with much higher accuracy than provided by a typical MR imaging process, in which gradient coil non-linearity is unaccounted for entirely, or only accounted for to low order. Thus, while not providing a signal that is apparent on an imaging data set, the tracking coils may provide information on a non-imaging data set that provides for improved geometric determination of devices associated with the tracking coils. In contrast, conventional techniques utilizing fiducial markers that show up on imaging data may compromise image quality in addition to providing less accurate geometric information. Thus, various embodiments provide for improved MR image quality and/or improved location of attenuating structures.

The information obtained via the tracking coil modules 124 in various embodiments may be used to correct attenuations in PET imaging data and/or MR imaging data. For example, attenuation correction information may be utilized by the PET reconstruction module 114 to correct PET imaging data. Additionally or alternatively, attenuation correction information may be used by the MR analysis module 128 to correct MR imaging data. It may be noted that the information obtained by the tracking coil modules 124 depicted in the illustrated embodiment may be used to correct attenuations in PET imaging data but not MR imaging data, as the depicted tracking coil modules 124 are disposed on surface coil modules 122. Because there is no need to correct for the presence of the surface coil modules 122 in MR images, information from tracking modules associated with the surface coil modules, for example, may be transmitted only to the PET reconstruction module 114 and not transmitted to or utilized by an MRI imaging analysis and/or reconstruction module.

In the illustrated embodiment, the depicted MR analysis module 128 includes a non-imaging analysis module 130 and an imaging analysis module 132. The non-imaging analysis module 130 obtains MR non-imaging information from the tracking coil modules 124. In various embodiments, the non-imaging analysis module 130 may determine the orientation and position of one or more external non-therapeutic structures associated with the tracking coil modules 124, and forward information corresponding to the position and orientation to the PET reconstruction module 114. In various embodiments, the non-imaging analysis module 130 may also provide information corresponding to attenuation properties of one or more external non-therapeutic structures 106 to the PET reconstruction module 114. Alternatively or additionally, the non-imaging analysis module 130 may provide information corresponding to the position and orientation (along with attenuation characteristic information, for example) to the imaging analysis module 132 and/or other aspect of the MR analysis module 128 for correction of MR imaging data to be used in reconstructing an MR image.

In the illustrated embodiment, the imaging analysis module 132 of the MRI analysis module 128 is configured to receive MR imaging information from the surface coil modules 122. In various embodiments, the imaging analysis module 132 is configured to receive attenuation information (e.g., information corresponding to an MRI attenuating structure within a field of view of a receive coil that is associated with a tracking coil), and to develop corrected MR imaging information for transmission to the MR reconstruction module 134. The MR reconstruction module 134 in turn is configured to reconstruct an MR image using MR imaging information (or corrected MR imaging information) corresponding to information obtained by the surface coil modules 124. Alternatively or additionally, the imaging analysis module 132 may be configured to transmit MR imaging information (or corrected MR imaging information) to the PET reconstruction module, which may in turn utilize the MR imaging information (or corrected MR imaging information) to correct PET imaging information for attenuation due to, for example, anatomical or other structures corresponding to the MR imaging information (or corrected imaging information). Thus, in various embodiments, the PET reconstruction module 114 may be configured to correct for an attenuation associated with the external non-therapeutic structure 106 (using information from the tracking coil modules 122 and/or the non-imaging analysis module 130), and also to correct an anatomical attenuation (using information from the surface coil modules 124 and/or the imaging analysis module 132).

Figure 2:
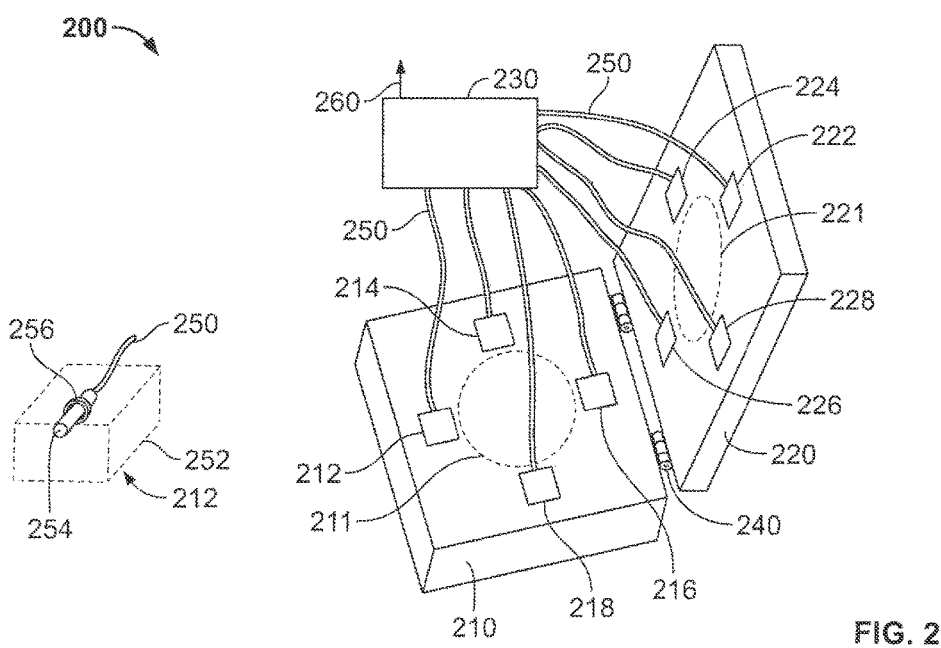
FIG. 2 is a schematic view of a tracking coil system in accordance with various embodiments.

FIG. 2 provides a schematic view of a tracking coil system 200 in accordance with various embodiments. In the illustrated embodiment, the tracking coil system 200 includes a first receive coil module 210 and a second receive coil module 220 joined by a hinge 240. The first receive coil module 210 and second receive coil module 220 joined by a hinge 240 provide an example of an external non-therapeutic structure that is articulable. Other types of devices may be utilized as articulable non-therapeutic structures and/or other articulation arrangements may be utilized in various embodiments. In the illustrated embodiment, the first receive coil module 210 and the second receive coil module 220 are configured as generally rigid bodies joined by a hinge; however, in alternate embodiments a flexible, conformable, or otherwise non-rigid structures may be employed, and/or other types of articulable joints or connections may be utilized.

Generally, in the illustrated embodiments, each of the receive coil modules 210, 220 includes a group of tracking coils mounted thereto, and an RF receive coil disposed therein. For example, an RF receive coil 211 is disposed within the first receive coil module 210. Tracking coils 212, 214, 216, 218 are disposed along a surface of the first receive coil 210. Because 3 points may be used to define the position and orientation of a rigid body, the total of four tracking coils 212, 214, 216, 218 provides a sufficient amount of data to determine the position and orientation of the first receive coil module 210, with an extra tracking coil for redundancy. Thus, by knowing the outline or shape of the first receive coil module 210 relative to the positions of the four tracking coils 212, 214, 216, 218 (e.g., by knowing where on the first receive coil module 210 the four tracking coils 212, 214, 216, 218 are mounted), the position and orientation of the first receive coil module 210 may be determined using the position of each of the four tracking coils 212, 214, 216, 218. Similarly, the second receive coil module 220 includes an RF receive coil 221 disposed therein. Also, tracking coils 222, 224, 226, 228 are disposed along a surface of the second receive coil 220. The depicted tracking coil system 200 also includes an analysis module 230 configured to receive information from the tracking coil modules, and to determine the position and orientation of the first receive coil module 210 and the second receive coil module 220 based on the position of the tracking coil modules.

For example, the position of tracking coils may be determined using a tracking pulse sequence including different passes taken at different orientations. In various embodiments, the sequence may have a dephasing gradient that is applied after an RF excitation pulse and before data acquisition, with the dephasing gradient applied for each readout orientation perpendicular to the frequency readout gradient. Various different orientations may be run in different orders in various embodiments. For example, in some embodiments, the orientations may be run in the following order: 1) Right-Left (e.g., in an x direction); 2) Anterior-Posterior (e.g., in a y direction); 3) Superior-Inferior (e.g., in a z direction); and 4) Inferior-Superior (e.g., in a negative z direction). The fourth aspect of the sequence (in a negative z direction) may be utilized to cancel out certain shifts. Other orientation sequences may be utilized in alternate embodiments. For example, in some embodiments, a sequence of Y, Z, X, −X may be employed. As another example, in some embodiments, a sequence of Z, X, Y, −Y may be employed. It may be noted that such sequences are not intended or configured for standard imaging, but instead to generate raw data files.

As indicated above, knowledge of at least 3 points of a rigid body may be sufficient to define the position and orientation of the rigid body. (As used herein, determining the position and orientation of a body may be understood as determining the location and boundaries of a volume occupied by the body in 3-dimensional space.) Thus, the position of 3 or more tracking coils may be used to define the position and orientation of an associated rigid receive coil module. For example, determination of the position of at least three of the tracking coils 212, 214, 216, 218 may be used to determine the position of the first receive coil module 210. Similarly, determination of the position of at least three of the tracking coils 222, 224, 226, 228 may be used to determine the position of the second receive coil module

220. Thus, in various embodiments, by associating a sufficient number of tracking coils with each articulable portion of a receive coil system (or other device or apparatus), the position of each articulable portion may be determined independently.

An enlarged view of the tracking coil 212 is shown on the left side of FIG. 2, with the exterior of the tracking coil 212 shown in phantom line and the interior of the tracking coil 212 visible. Each of the tracking coils depicted in FIG. 2 may be configured similarly to the arrangement shown for the tracking coil 212. As shown in FIG. 2, the tracking coil 212 includes a body 252, a reservoir 254, a coil 256 and a cable 250. The reservoir 254 and coil 256 are disposed with the body 252. The reservoir 254 is configured to contain a fluid, and the coil 256 is disposed around the reservoir 254. The coil 256 may be used to detect or sense the presence of the fluid within the reservoir 254 during a MR scan, and the position of the tracking coil 212 may thus be determined.

As shown in FIG. 2, each tracking coil 212, 214, 216, 218, 222, 224, 226, 228 may be communicably coupled with the analysis module 230 with a cable 250. The analysis module 230 in the illustrated embodiment is configured to recognize each particular tracking coil (for example, via an electronic signature), and to analyze the position of groups of tracking coils to determine the position and orientation of a corresponding external non-therapeutic structure (e.g., first receiving coil module 210, second receiving coil module 220). In various embodiments, the analysis module 230 may include a memory having a database, or have access to a database including information correlating tracking coils with outlines or shapes of corresponding structures, as well as the position of particular tracking coils on the corresponding structures. The analysis module 230 may determine the position of the corresponding structures using the information from the data base along with the position of particular tracking coils as determined using information from the tracking coils.

For example, the analysis module 230 may receive information from the tracking coils 212, 214, 216, and 218, and determine the position of the tracking coils 212, 214, 216, and 218. Then, the analysis module 230 may access a database providing information correlating the position of the tracking coils with the position of the first receiving coil module 210, and determine the position and orientation of the first receiving coil module 210 based on the position of the tracking coils 212, 214, 216, and 218. Further, the analysis module 230 may access a database correlating attenuation properties with the first receiving coil 210, and transmit information 260 including information corresponding to the position of the first receiving coil 210 as well as the attenuation properties or characteristics of the first receiving coil 210 to a non-MR imaging system (e.g., first imaging acquisition system 110) for correcting attenuation due to the second receive coil module 210. Similarly, the attenuation in a non-MR image (e.g., PET, SPECT, or CT, among others) may be determined for the second receive coil module 220 and/or other or additional external non-therapeutic structures.

Alternatively or additionally to articulating structures, in various embodiments the position and orientation of deformable or conformable structures may be determined, and the attenuation due to such structures accounted for in a non-MR imaging system. FIG. 3 provides a front view of a pad 300 that is an example of an external non-therapeutic structure configured as a deformable, flexible, conformable, or otherwise non-rigid body, in accordance with various embodiments. FIG. 4 shows a side view of the pad 300 in a first position, and FIG. 5 shows a side view of the pad 300 in a second position in which the pad has been deformed relative to the first position (e.g., the position depicted in FIG. 4.) The pad 300 is configured to be non-rigid or deformable. For example, a surface of the pad in contact with a patient may change shape to conform with the outside of the patient, providing improved comfort relative to a rigid structure. By way of example, in various embodiments, the pad 300 may be configured as a patient comfort pad and used to support and/or position a patient during a scanning procedure. As another example, in other embodiments, one or more RF receive coils may be disposed within the pad 300, and the pad 300 may be configured as or be a portion of an RF receive coil module.

As seen in FIG. 3, the depicted pad 300 includes a surface 312. An array 320 of tracking coils 326 are disposed on the surface 312, and configured to provide information corresponding to the position of various portions of the surface 312. Each of the tracking coils may be understood as providing a grid point of the surface 312. The location of each coil or grid point may be used to create a topographic representation of the surface 312 used to define the position and orientation of the pad 300. By determining the position of each of the tracking coils 326, a 3-dimensional map of the grid points or a topographic map corresponding to the contour of the surface 312 at a given time may be determined and used to determine a shape or profile of the surface 312. In the illustrated embodiment, the tracking coils 326 are arranged in three rows 322 and four columns 324. Other arrangements may be utilized in other embodiments. For example, additional tracking coils may be positioned on additional surfaces, and/or other patterns or arrays of tracking coils may be employed. Generally, the more complex contours or shapes that the pad 300 is capable of, the more tracking coils may be employed.

For example, when the pad 300 is in the first position depicted in FIG. 4, the positions of the various tracking coils 326 may be determined to be substantially co-planar. Thus, the surface 312, to which the tracking coils 326 are mounted, may be determined to be substantially planar. However, when the pad 300 is deformed to the second position shown in FIG. 5, the position of the various tracking coils 326 may define a substantially rounded profile. Thus, the surface 312 may be determined to have a rounded or concave shape as shown in FIG. 5. It may be noted that the particular deformation of FIG. 5 is configured for clarity and ease of illustration, and that more complicated or complex topographies or profiles of the surface 312 may be determined as well. In various embodiments, the surface 312 may take on a more complicated contour, and the surface 312 may be characterized by one or more compound curves, depressions, protrusions, or the like.

Figure 6:
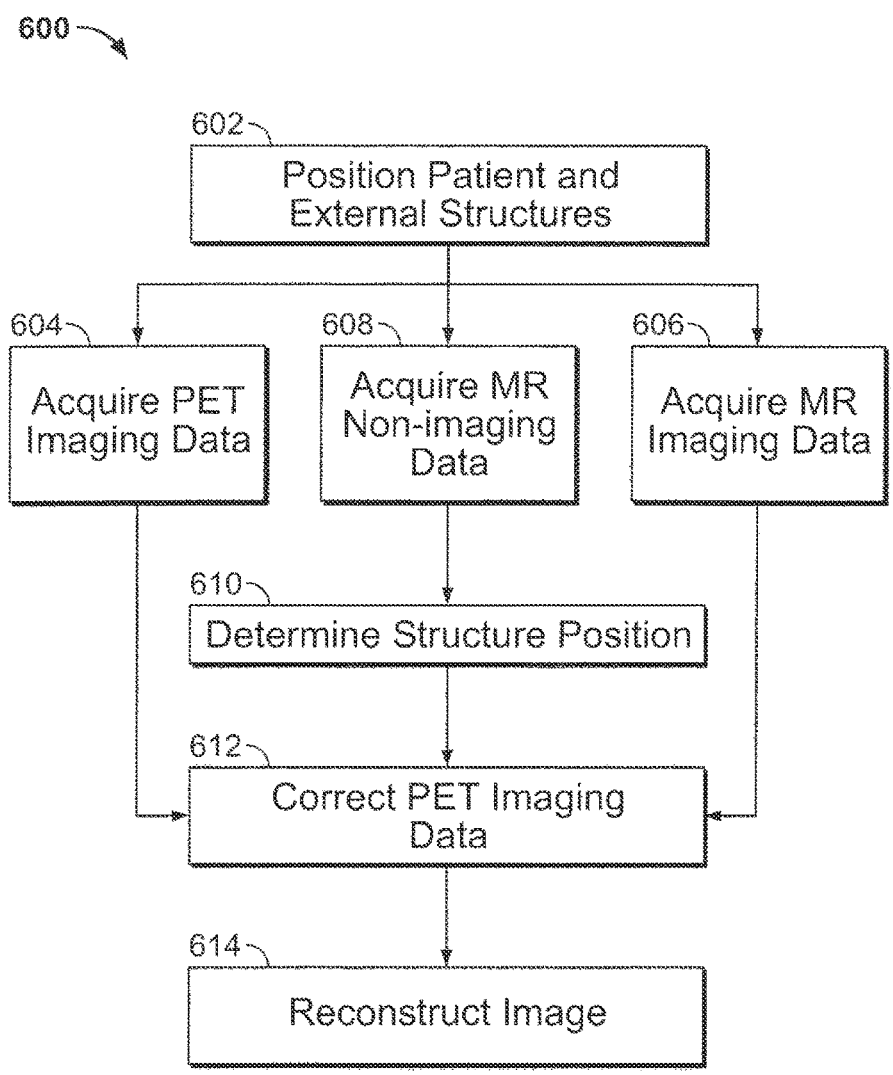
FIG. 6 is a flowchart of a method of imaging in accordance with various embodiments.

FIG. 6 provides a flowchart of a method 600 for imaging an object. In various embodiments, the method 600, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 600 may be able to be used as one or more algorithms to direct hardware to perform operations described herein.

At 602, a patient and one or more external non-therapeutic structures are positioned. The non-therapeutic structures are not integral to the MRI system housing, nor part of the PET system housing. The non-therapeutic structures may be separate and distinct from (and moveable in various directions and orientations relative to) the housing of the MRI system, the housing of the PET system, and the patient table. For example, the non-therapeutic structures may be MR surface coils, the patient support, and positioning pads. For example, external non-therapeutic structures may include one or more of patient comfort pads placed against a patient, audio-visual equipment configured to help a patient relax or remain calm, gating detections devices such as ECG measurement equipment, or RF receive coils configured for use with MR imaging. One or more of the external non-therapeutic structures may be rigid, while one or more may be articulable and/or deformable. Each external non-therapeutic structure may be associated with a sufficient number of MR tracking coils to define the position of the structure (e.g., the boundaries of a volume occupied by the structure). For example, a group of tracking coils may be mounted or affixed to one or more surfaces of the external non-therapeutic structure. Attenuation characteristics of each structure as well as the position of associated tracking coils relative to the shape or outline of the structure may be stored in a database and used to determine the position of the structure based on the determined position of the associated tracking coils, as well as the attenuation effects the structure has on one or more sets of imaging data. In various embodiments, additional tracking coils associated with internal and/or therapeutic devices may be positioned as well. As used herein, an internal structure, body, or device, may be understood as a structure that is configured to be positioned partially or entirely inside of or within an exterior of an object being imaged during at least a portion of an imaging procedure.

Optionally, at 602, one or more reference coordinate systems are defined, for example relative to a coordinate system based on an origin reference point on the MRI system, PET system and the like.

At 604, PET imaging data is acquired. The PET imaging data may be acquired for example, via one or more acquisition modules include an array of detectors, such as detectors formed in one or more rows of rings. The detectors may be configured to detect annihilation events associated with a radiopharmaceutical that has been introduced to the patient.

At 606, MR imaging data is acquired. The MR imaging data may be acquired using one or more acquisition modules including RF receive coils disposed proximate a patient or a portion of a patient, with the RF receive coils configured to detect NMR activity.

At 608, MR non-imaging, non-patient data (also referred to as "foreign structure data" or "FS data") is acquired. The MR non-imaging or FS data may be acquired via the use of MR tracking coils that obtain information used to address attenuations, but not configured to be used as patient imaging data. The MR non-imaging or FS data may correspond to the position of one or more MR tracking coils associated with (e.g., mounted to or otherwise affixed to) an external non-therapeutic structure. For example, the FS data may provide coordinates, within a predefined three dimensional coordinate system, for one or more reference points on the non-therapeutic structure. In various embodiments, a sequence of pulses may be employed to determine the position of one or more MR tracking coils. In some embodiments, the MR tracking coils may be configured to provide data not used directly for imaging. For example, the MR tracking coils may use relatively small reservoirs of liquid and may not appear on an MR image, but provide improved geometric accuracy relative to imaging data. As discussed herein, the MR non-imaging data may be used to determine the position and orientation of one or more external non-therapeutic structures, and to account for the attenuation due to the one or more external non-therapeutic structures in a non-MR (e.g., PET, SPECT) imaging modality.

At 610, the position and orientation of one or more external non-therapeutic structures is determined. For example, the detected or otherwise determined position of one or more tracking coils along with a priori knowledge or information regarding the distribution or positioning of the one or more tracking coils with respect to a given structure may be used to determine the position and orientation of a given structure. The position and orientation of a given structure may be performed on a cyclic, periodic, iterative, or otherwise ongoing basis to help determine or monitor any changes in a position, articulation, and/or deformation of the structure.

At 612, the PET imaging data is corrected. For example, the PET imaging data may be corrected to account for or address an attenuation associated with one or more external non-therapeutic structures. For example, the position of a structure as determined at 610 may be used in connection with PET attenuation characteristics of the structure to correct the PET imaging data and provide corrected PET imaging data accounting for the attenuation due to one or more external non-therapeutic structures. Additionally, in some embodiments, MR imaging data (e.g., imaging data obtained at 606) may be used to correct the PET imaging data, for example, for attenuation due to one or more anatomical features corresponding to the MR imaging data.

At 614, an image (e.g., a PET image) is reconstructed. The image may be reconstructed using corrected PET imaging data (e.g., PET imaging data corrected at 612 to account for attenuation due to one or more external non-therapeutic structures). In various embodiments, the reconstructed image may combined with an MR image to provide an image based on PET imaging data as well as anatomy identified by MR imaging techniques.

Figure 7:
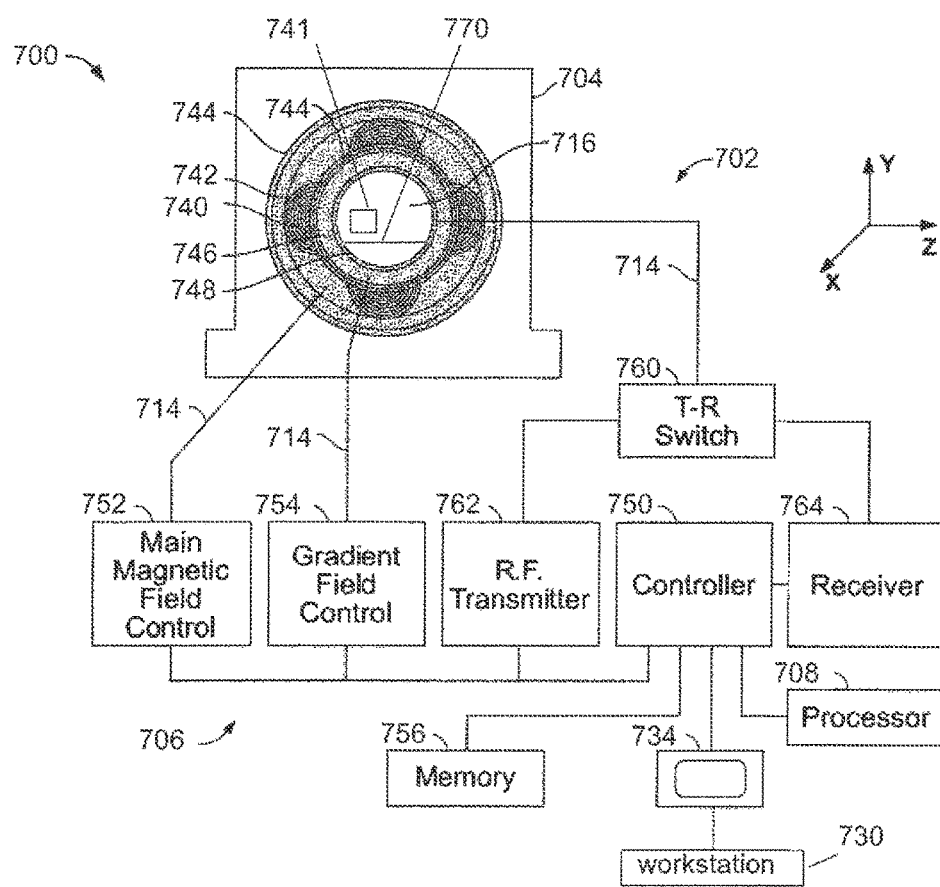
FIG. 7 is a schematic illustration of an exemplary MRI medical imaging system in accordance with various embodiments.

Various embodiments described herein may be used in conjunction with a medical imaging system, such as the imaging system 700 shown in FIG. 7. It should be appreciated that although the imaging system 700 is illustrated as a single modality imaging system for ease of illustration of that particular modality, the various embodiments may be implemented in or with multi-modality imaging systems. The imaging system 700 is illustrated as an MRI imaging system. Moreover, the various embodiments are not limited to medical imaging systems for imaging human subjects, but may include veterinary or non-medical systems for imaging non-human objects, luggage, etc.

Referring to FIG. 7, the imaging system 700 includes an imaging portion 702 having an imaging unit 704 (e.g., imaging scanner) and a processing portion 706 that may include a processor 708 or other computing or controller device. In particular, the imaging unit 704 enables the imaging system 700 to scan an object or patient to acquire image data, which may be image data of all or a portion of the object or patient. The imaging unit 704 includes one or more imaging components that allow acquisition of image data. The imaging components produce signals that represent image data that is communicated to the processing portion 706 via one or communication links 714 that may be wired or wireless. The patient may be positioned within a bore 716 using, for example, a motorized table and then MR imaging performed as described in more detail herein.

In operation, an output of one or more of the imaging components is transmitted to the processing portion 706, and vice versa, which may include transmitting signals to or from the processor through a control interface, which may be embodied as a system interface. The processor 708 also may generate control signals for controlling the position of the motorized table or imaging components based on user inputs or a predetermined scan. For example, RF signals or transmit pulses may be communicated through the one or more communication link 714.

During a scan, image data, such as magnetic resonance image data from the imaging components may be communicated to the processor 708 through a data interface via the control interface, for example, as acquired by a body coil or surface coil.

The processor 708 and associated hardware and software used to acquire and process data may be collectively referred to as a workstation. The workstation 730 may include, for example, a keyboard and/or other input devices such as a mouse, a pointer, and the like, and a monitor 734. The monitor 734 displays image data and may accept input from a user if a touchscreen is available.

In the exemplary embodiment, the imaging system 700 also includes a superconducting magnet 740 formed from magnetic coils supported on a magnet coil support structure. However, in other embodiments, different types of magnets may be used, such as permanent magnets or electromagnets. A vessel 742 (also referred to as a cryostat) surrounds the superconducting magnet 740 and is filled with liquid helium to cool the coils of the superconducting magnet 740. A thermal insulation 744 is provided surrounding the outer surface of the vessel 742 and the inner surface of the superconducting magnet 740. A plurality of magnetic gradient coils 746 are provided within the superconducting magnet 740 and an RF transmit coil 748 is provided within the plurality of magnetic gradient coils 746. The components within a gantry generally form the imaging portion 702. It should be noted that although the depicted superconducting magnet 740 is a cylindrical shaped, other shapes of magnets can be used.

The processing portion 706 also generally includes a controller 750, a main magnetic field control 752, a gradient field control 754, a memory 756, the display device 734, a transmit-receive (T-R) switch 760, an RF transmitter 762 and a receiver 764.

In operation, a body of an object, such as the patient or a phantom to be imaged, is placed in the bore 716 on a suitable support, for example, a motorized table or other patient table, such as the patient table 770. The superconducting magnet 740 produces a uniform and static main magnetic field $B_o$ across the bore 716. The strength of the electromagnetic field in the bore 716 and correspondingly in the patient, is controlled by the controller 750 via the main magnetic field control 752, which also controls a supply of energizing current to the superconducting magnet 740.

The magnetic gradient coils 746, which include one or more gradient coil elements, are provided so that a magnetic gradient can be imposed on the magnetic field $B_o$ in the bore 716 within the superconducting magnet 740 in any one or more of three orthogonal directions x, y, and z. The magnetic gradient coils 746 are energized by the gradient field control 754 and are also controlled by the controller 750.

The RF transmit coil 748 is arranged to transmit RF magnetic pulses and/or optionally detect MR signals from the patient if receive coil elements are not provided. In the illustrated embodiment, a receive coil 741 is provided to detect MR signals. A single receive coil 741 is depicted schematically in FIG. 7; however, more than one receive coil 741 may be employed. In various embodiments, the receive coil 741 may be configured to conform to a portion of the patient (e.g., head) and to detect MR signals from that portion of the patient. The RF transmit coil 748 and the receive coil(s) are selectably interconnected to one of the RF transmitter 762 or receiver 764, respectively, by the T-R switch 760. The RF transmitter 762 and T-R switch 760 are controlled by the controller 750 such that RF field pulses or signals that are generated by the RF transmitter 762 are selectively applied to the patient for excitation of magnetic resonance in the patient.

Following application of the RF pulses, the T-R switch 760 is again actuated to decouple the RF transmit coil 748 from the RF transmitter 762. The detected MR signals are in turn communicated to the controller 750. The controller 750 includes a processor (e.g., image reconstruction processor), for example the processor 708, that controls the processing of the MR signals to produce signals representative of an image of the patient.

The processed signals representative of the image are also transmitted to the display device 734 to provide a visual display of the image. Specifically, the MR signals fill or form a k-space that is Fourier transformed to obtain a viewable image. The processed signals representative of the image are then transmitted to the display device 734.

Figure 8:
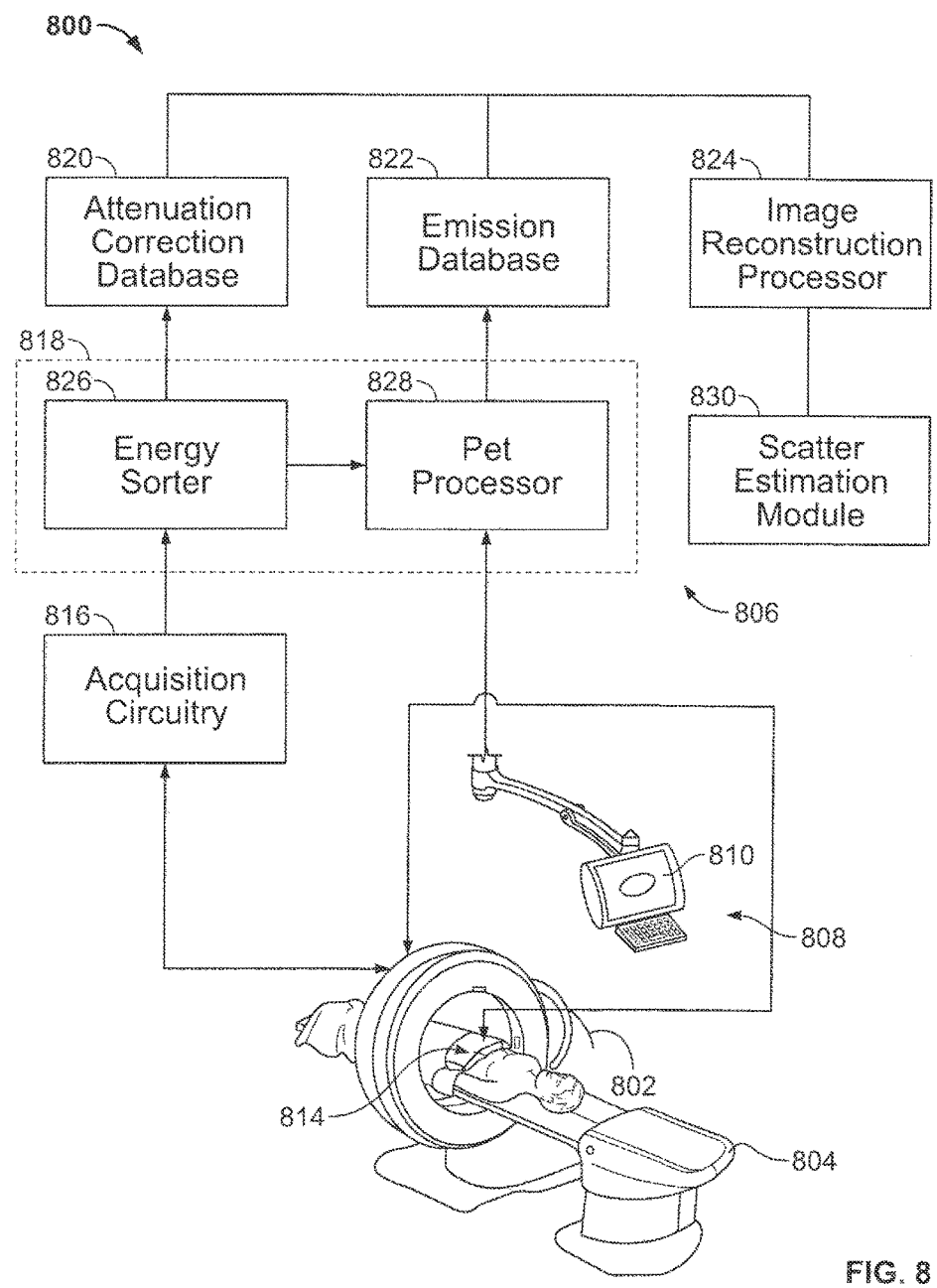
FIG. 8 is a schematic illustration of an exemplary PET medical imaging system in accordance with various embodiments.

The various embodiments may be implemented, for example, in conjunction with a medical imaging system 800 illustrated in FIG. 8, which is shown as a PET system that includes MR imaging capabilities, for example, configured as a multi-modality imaging system, such as a PET/MR imaging system. However, it should be appreciated that various embodiments may be implemented in connection with other modalities additionally or alternatively. Moreover, the imaging detectors may be of different types and configurations.

Thus, in one embodiment, the medical imaging system 800 is a PET/MR imaging system as illustrated in FIG. 1. It should be noted that in some embodiments, the MR data may be acquired simultaneously and/or concurrently with the PET data. However, the data may be acquired in different orders and combinations thereof (e.g., in an interleaved manner).

The medical imaging system 800 generally includes a gantry 802, a patient table 804, and a processing and control system 806 including a user input 808 with a display 810. The gantry 802 provides mechanical support for imaging devices such as, for example, detectors, scanners and transmitters that are used for scanning a patient or other object (e.g., a phantom). The gantry 802 houses imaging devices such as, for example, PET detectors or x-ray detectors. It should be noted that the PET portion of the system in one embodiment is a stationary annular detector, namely a ring of detectors.

The imaging devices on the gantry 802 acquire image data by scanning a patient or other object on the patient table 804. Moving the patient table 804 enables the scanning of various portions of the patient or object. The patient table 804 lies along the axis of the gantry 802, which is known as a viewing area along an examination axis and can be moved along this axis. The patient table 804 can be positioned at various axial positions along the axis. In some embodiments, the gantry 802 includes a plurality of PET detectors that are fixed and spaced on gantry 802, which are positioned radially outward from the axis and that may be configured as one or more rings of detectors. In accordance with other embodiments, the gantry 802 includes a plurality of detectors that are rotatable about the axis. For MR imaging, such as to acquire attenuation information, a receive coil 814 may be placed proximal a portion of interest of the patient. Additional details regarding MR imaging systems are provided in connection with the discussion of FIG. 7 herein.

The processing and control system 806 controls the positioning of the patient table 804, as well as receiving data acquired during scanning. In various embodiments, the processing and control system 806 controls the medical imaging system 800 to acquire, for example, image information and/or attenuation information of a volume of interest, for example, a patient and as described in more detail herein. For example, annihilation events may be detected as emission data (e.g., emitted from a patient injected with a radionuclide).

Various processors, sorters, and databases are used to acquire and manipulate emission data, which is used in accordance with various embodiments. The processors, sorters and databases of FIG. 8 include acquisition circuitry 816, an acquisition processor 818, an attenuation correction database 820, an emission database 822, and an image reconstruction processor 824. The acquisition processor 818 is programmed to acquire emission data, for example, in a list mode and/or a sinogram mode, as described in more detail below, and generate an image based on the emission data acquired in the list mode and/or the emission data acquired in the sinogram mode, which is scatter corrected. The medical imaging system 800 may also include other computing components. The attenuation correction database 820 may include attenuation map data derived from, as one example, MR data, or, as another example, CT data.

In some embodiments, an energy sorter 826 provides, for example, time, location, and energy data to a PET processor 828. The PET processor 828 generally uses the received data to identify pairs of data, also known as coincidence pairs, coincident pair lines and lines of response, corresponding to annihilation events that occurred inside the region of interest. After the acquisition processor 818 identifies an annihilation event, the acquisition processor 818 updates data in the emission data database 822 to store information relating to the annihilation events.

Thus, after an acquisition session has been completed and sets of data have been stored in one or more databases, the image reconstruction processor 824 accesses the data in the databases 820 and 822 and uses the accessed data to generate images that may be requested by a system operator. Additionally, the sets of transmission and emission data are used by a scatter estimation module 830 to perform scatter estimation, particularly multiple scatter estimation (e.g., estimating multiple 3D PET scatter) as described in more detail herein.

It should be noted that the reconstruction of the emission data may be performed in any suitable manner using any type of image reconstruction process, such as analytical image reconstruction algorithms known in the art. In one embodiment, the images are reconstructed from the scan of the patient or object correcting for multiple scatters using a convolution method having a kernel with an amplitude and width that varies as a function of a filtered attenuation sinogram.

Thus, various embodiments provide improved location determination of attenuating objects and improved accounting for attenuation due to attenuating objects. Various embodiments also provide for improved quantitation of PET imaging data, reduction of artifacts, and image quality.

It should be noted that the particular arrangement of components (e.g., the number, types, placement, or the like) of the illustrated embodiments may be modified in various alternate embodiments. In various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), a given module or unit may be added, or a given module or unit may be omitted.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and the like. The storage device may also be other similar means for loading computer programs or other instructions into the computer or processor.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A system for imaging a portion of a patient within a field of view (FOV) of the system, comprising:
a first imaging acquisition module comprising at least one of a PET, SPECT, or CT detector, the first imaging acquisition module configured to acquire imaging information for the portion of the patient within the FOV using a non-MRI first modality;
a magnetic resonance imaging (MRI) acquisition module including an array of tracking coils that are configured to acquire magnetic resonance (MR) information associated with an external non-therapeutic (ENT) structure within the FOV, the MR information comprising MR non-imaging, foreign structure (NIFS) information associated with the ENT structure, wherein the ENT structure comprises a pad having a deformable surface, wherein the array of tracking coils are disposed on the deformable surface of the pad, each tracking coil corresponding to a grid point of the deformable surface, the MR NIFS information corresponding to a contour of the deformable surface and a position and orientation of the ENT structure; and
a first reconstruction module comprising at least one processor and configured to reconstruct an image using the imaging information acquired by the first imaging acquisition module, wherein the first reconstruction module is configured to obtain the MR NIFS information and use the MR NIFS information to correct for attenuation associated with the ENT structure, wherein the first reconstruction module is configured to determine a corresponding position of each tracking coil and use the determined positions of the tracking coils to create a topographic representation of the contour of the deformable surface using the MR NIFS information to define a shape of the deformable surface, wherein the first reconstruction module is configured to determine the positions for the tracking coils using a tracking pulse sequence comprising different passes taken at corresponding different orientations in the following order: in a first direction, in a second direction oriented at 90 degrees to the first direction, in a third direction oriented at 90 degrees to the first direction and the second direction, and in a fourth direction opposite to the third direction.

2. The system of claim 1, wherein the first imaging acquisition module is configured to obtain positron emission tomography (PET) information, and wherein the first reconstruction module is configured to reconstruct a PET image using the PET information.

3. The system of claim 1, wherein the ENT structure comprises first and second portions that are articulable with respect to each other, wherein the system comprises plural groups of tracking coils disposed along corresponding surfaces of the first and second portions.

4. The system of claim 1, wherein the array comprises at least three rows and four columns.

5. The system of claim 1, wherein the MR information includes MR imaging information associated with the portion of the patient in the FOV and configured for use in reconstructing an MR image of the portion of the patient within the FOV, wherein the MR imaging information is acquired via at least one receive coil disposed within the ENT structure, wherein the first reconstruction module is configured to correct an attenuation associated with the at least one receive coil.

6. The system of claim 1, wherein the first reconstruction module is configured to utilize the MR imaging information to correct an anatomical attenuation.

7. A method of imaging an object comprising:
acquiring, with a first imaging acquisition module comprising at least one of a PET, SPECT, or CT detector, first imaging information corresponding to a non-MRI first modality;
acquiring, with a magnetic resonance imaging (MRI) acquisition module including an array of tracking coils, magnetic resonance (MR) non-imaging, foreign structure (NIFS) information associated with an external non-therapeutic (ENT) structure, wherein the ENT structure comprises a pad having a deformable surface, wherein the pad comprises the array of tracking coils, the array of tracking coils disposed on the deformable surface of the pad, wherein, the MR NIFS information is acquired via the array of tracking coils, each tracking coil corresponding to a grid point of the deformable surface, the MR NIFS information corresponding to a contour of the deformable surface a position and orientation of the ENT structure;

addressing an attenuation in the first imaging information associated with the ENT structure to produce corrected first imaging information, wherein the attenuation is addressed using the MR NIFS information, wherein addressing the attenuation comprises determining a corresponding position of each tracking coil and using the determined positions of the tracking coils to create topographic representation of the contour of the deformable surface using the MR NIFS information to define a shape of the deformable surface, wherein determining the corresponding position of each tracking coil comprises using a tracking pulse sequence comprising different noses taken at corresponding different orientations in the following order: in a first direction, in a second direction oriented at 90 degrees to the first direction, in a third direction oriented at 90 degrees to the first direction and the second direction, and in a fourth direction opposite to the third direction; and reconstructing, with a first reconstruction module, an image using the corrected first imaging information.

8. The method of claim 7, wherein the first imaging acquisition module is configured to obtain positron emission tomography (PET) information, and wherein the first reconstruction module is configured to reconstruct a PET image using the PET information.

9. The method of claim 7, wherein the ENT structure comprises first and second portions that are articulable with respect to each other, wherein the system comprises plural groups of tracking coils disposed along corresponding surfaces of the first and second portions.

10. The method of claim 7, wherein the array comprises at least three rows and four columns.

11. The method of claim 7, wherein the MRI acquisition module includes at least one receive coil configured to obtain MR imaging information for use in reconstructing an MR image, wherein the at least one receive coil is disposed within the ENT structure, wherein the addressing the attenuation comprises addressing an attenuation associated with the at least one receive coil.

12. The method of claim 7, wherein the MRI acquisition module includes at least one receive coil configured to obtain MR imaging information for use in reconstructing an MR image, wherein the addressing the attenuation comprises addressing an anatomical attenuation using the MR imaging information.

13. A tangible and non-transitory computer readable medium comprising one or more computer software modules configured to direct one or more processors to:

obtain first imaging information corresponding to a non-MRI first modality;

obtain magnetic resonance (MR) non-imaging, foreign structure (NIFS) information associated with an external non-therapeutic (ENT) structure, wherein the ENT structure comprises a pad having a deformable surface, wherein the MR NIFS information is acquired via an array of tracking coils disposed on the deformable surface of the pad, each tracking coil corresponding to a grid point of the deformable surface, the MR NIFS information corresponding to a contour of the deformable surface and a position and orientation of the ENT structure;

address an attenuation in the first imaging information associated with the ENT structure to produce corrected first imaging information, wherein the attenuation is addressed using the MR NIFS information, wherein addressing the attenuation comprises determining a corresponding position of each tracking coil and using the determined positions of the tracking coils to create a topographic representation of the contour of the deformable surface using the MR NIFS information to define a shape of the deformable surface, wherein the one or more computer software modules are configured to direct the one or more processors to determine the positions for the tracking coils using a tracking pulse sequence comprising different passes taken at corresponding different orientations in the following order: in a first direction, in a second direction oriented at 90 degrees to the first direction, in a third direction oriented at 90 degrees to the first direction and the second direction, and in a fourth direction opposite to the third direction; and reconstruct an image using the corrected first imaging information.

14. The computer readable medium of claim 13, wherein the one or more computer software modules are further configured to direct the one or more processors to obtain positron emission tomography (PET) information, and wherein the computer readable medium is further configured to direct the one or more processors to reconstruct a PET image using the PET information.

15. The computer readable medium of claim 13, wherein the ENT structure comprises first and second portions that are articulable with respect to each other, wherein the system comprises plural groups of tracking coils disposed along corresponding surfaces of the first and second portions, wherein the one or more computer software modules are further configured to direct the one or more processors to obtain the MR NIFS information from the plural groups of tracking coils.

16. The computer readable medium of claim 13, wherein the array comprises at least three rows and four columns.

17. The computer readable medium of claim 13, wherein at least one receive coil configured to obtain MR imaging information for use in reconstructing an MR image is disposed within the ENT structure, wherein the attenuation addressed comprises an attenuation associated with the at least one receive coil, wherein the one or more computer software modules are further configured to direct the one or more processors to address the attenuation associated with the at least one receive coil.

* * * * *